United States Patent [19]

Wagner et al.

[11] Patent Number: 4,563,635
[45] Date of Patent: Jan. 7, 1986

[54] MOISTURE MEASURING METHOD AND APPARATUS

[76] Inventors: Delmer W. Wagner, Edward D. Wagner, both of 392 Pine Grove Rd., R.R., Rogue River, Oreg. 97537

[21] Appl. No.: 494,953

[22] Filed: May 16, 1983

[51] Int. Cl.⁴ .......................................... G01R 27/26
[52] U.S. Cl. ................... 324/61 R; 324/65 R; 406/88
[58] Field of Search ............... 406/88; 271/97, 195; 324/61 R, 65 R, 57 R; 340/870.37

[56] References Cited

U.S. PATENT DOCUMENTS

| | | | |
|---|---|---|---|
| 3,732,553 | 5/1973 | Hardway | 340/870.37 |
| 3,815,021 | 6/1974 | Kerr | 324/61 R |
| 3,990,005 | 11/1976 | Abbe | 324/61 R |
| 4,081,201 | 3/1978 | Hassan | 406/88 |
| 4,092,579 | 5/1978 | Weit | 324/61 R |
| 4,377,783 | 3/1983 | Wagner | 324/61 R |

FOREIGN PATENT DOCUMENTS

| | | | |
|---|---|---|---|
| 2507833 | 9/1976 | Fed. Rep. of Germany | 406/88 |
| 3328421 | 2/1984 | Fed. Rep. of Germany | 324/61 R |

OTHER PUBLICATIONS

Gagne: "Device Air Transport System"—IBM Tech. Disc. Bull., Jun. 1978—pp. 84–85.

Primary Examiner—Stanley T. Krawczewicz
Assistant Examiner—Jose M. Solis
Attorney, Agent, or Firm—John P. Dellett

[57] ABSTRACT

Moisture in wood veneer strips received from a drying oven is measured by passing the veneer strips on a conveyor between arrays of plates including a transmitting plate on one side of the veneer and a juxtaposed receiving plate on the other. Phase plates on either side of and on the same level as the transmitting plate are empowered by a signal having the reverse phase to that applied to the transmitting plate, and when wet veneer passes between the plate arrays, part of the transmitted signal is shunted, placing the veneer at virtual ground level and reducing the signal received by the receiving plate. A plurality of diagonal passages in the lower plate array receive air under pressure for conveying the veneer strips thereover.

25 Claims, 6 Drawing Figures

U.S. Patent  Jan. 7, 1986  4,563,635
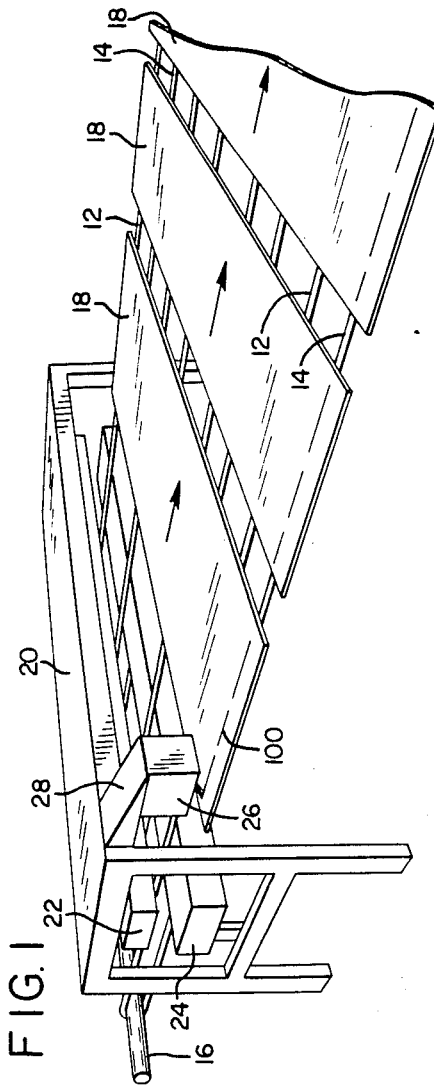
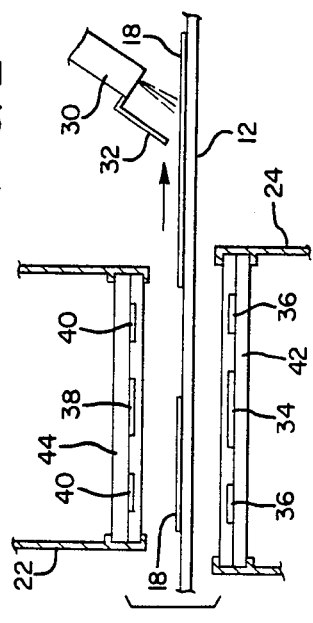
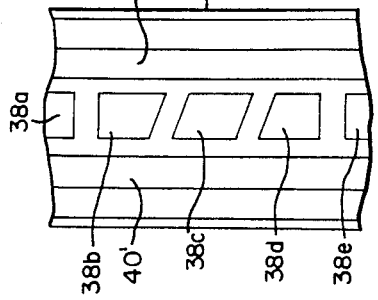
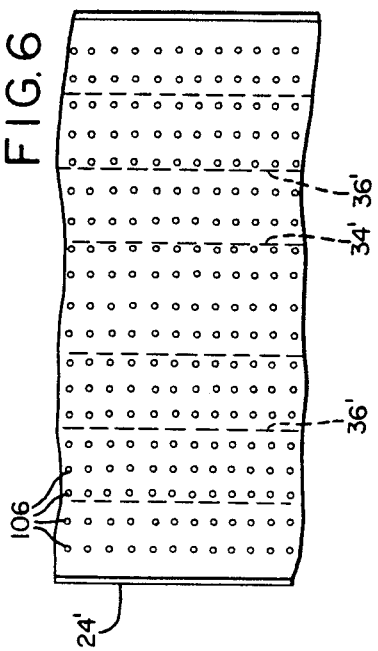
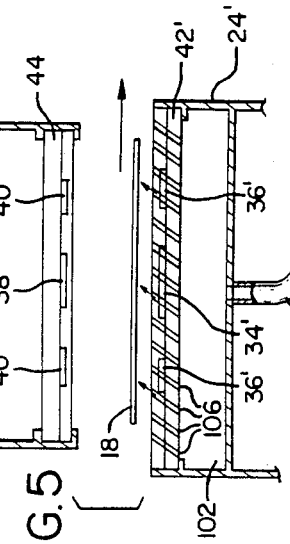
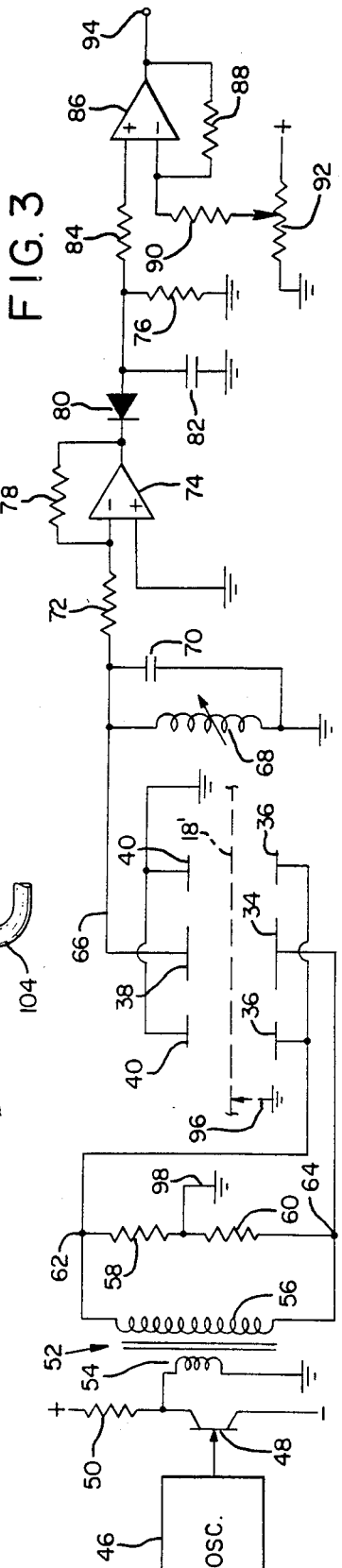

MOISTURE MEASURING METHOD AND APPARATUS

BACKGROUND OF THE INVENTION

The present invention relates to a method and apparatus for measuring moisture, and particularly to an improved method and apparatus which is less sensitive to the positioning of material in which the moisture is to be measured than prior art devices.

Moisture measuring devices of the prior art typically employ some kind of contacting means for making a conductive connection with material in which moisture is to be measured so that the moisture can be determined by electrical conduction. Unfortunately, the contacting means or brushes are subject to breakage and shorting whereby the moisture indications tend to become inaccurate. Further, even if the brushes are in good condition, the degree of electrical contact provided with the material under test is non-uniform.

Moisture detectors have been developed which do not require contact with the material but instead employ capacitive coupling or the like. Many, however, are quite sensitive to the position of the material relative to the sensor conductor, as well as to the thickness of the material, and therefore indications derived on a production line basis can be somewhat undependable. Also, the conveying means upon which the material is transported can short out the measuring system such that a dependable reading is not obtained.

In my prior U.S. Pat. No. 4,377,783, a measuring system is set forth in which transmitting and receiving plates are offset along the path of the measured material, and a conductive path in the veneer and the grounded conveyor is employed as part of the circuit. While very efficacious, there is again some dependency upon accurate contact with the material being measured. It would also be desirable to provide a moisture measuring method and apparatus which is almost entirely independent of positioning of the material so that the measurement is even less subject to such factors as warp, thickness and the like. Almost all prior art devices have some dependence upon these factors, and also to unwanted grounding of the material as mentioned above.

SUMMARY OF THE INVENTION

According to the present invention, in a preferred embodiment thereof, the material, e.g. wood veneer, is transported along a path into a region between a transmitting conductor means and a receiving conductor means that are relatively juxtaposed to one another. Third conductor means adjacent but laterally spaced from the transmitting conductor means are empowered in out-of-phase relation with the transmitting conductor means such that in the presence of moist material, the transmitting signal tends to be diverted to the third conductor means, with the moist material acting as a shield, substantially at ground potential, in front of the receiver conductor means. The reduction in signal received at the receiver conductor means is employed as an indication of moisture, and it is found this system is highly independent of the position of the material relative to conductor means. Furthermore, inasmuch as the moist material is driven to approximate ground level, the position thereof has little influence on the receiver circuits, and moreover accidental or intentional grounding of the moist material has little effect on the output measurement.

In accordance with an embodiment of the present invention, conveyor means for transporting material between transmitter and receiver conductor means comprises a plurality of air passages underneath the conveyed material providing an upwardly directed air pressure cushion. These passages desirably slant forwardly in the direction of desired movement whereby to convey the material.

It is accordingly an object of the present invention to provide an improved moisture detector for detecting moisture in plywood veneer or other material.

It is a further object of the present invention to provide an improved apparatus for moisture detection wherein such apparatus is economical in construction and reliable in operation.

It is another object of the present invention to provide an improved moisture detecting method and apparatus which is largely independent of positioning of the material relative to sensing means.

It is a further object of the present invention to provide an improved method and apparatus for moisture detection which is substantially insensitive to accidental grounding of moist material.

It is a further object of the present invention to provide improved conveyor means for a detecting apparatus.

The subject matter which we regard as our invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

FIG. 1 is a perspective view of moisture detecting apparatus according to the present invention;

FIG. 2 is a longitudinal cross-sectional view of such apparatus;

FIG. 3 is a schematic diagram of circuitry according to the moisture detecting method and apparatus of the present invention;

FIG. 4 is a bottom view of an upper cabinet of the moisture detecting apparatus according to a variation of the present invention suitable for longitudinal feed of a plurality of veneer strips or the like;

FIG. 5 is a longitudinal cross-sectional view of moisture detecting apparatus according to another embodiment of the present invention including means for providing an air cushion conveyor for transporting the material, the moisture of which is to be ascertained; and FIG. 6 is an enlarged top view of the lower cabinet in FIG. 5, showing the plurality of passage openings for providing a conveying air cushion.

DETAILED DESCRIPTION

Referring to the drawings and particularly to FIGS. 1-3, illustrating moisture detecting apparatus according to the present invention, a conveyor comprising upper parallel runs 12 and lower return runs 14, suitably comprising chains or belts, pass around an end shaft schematically illustrated at 16. The end shaft 16 may incorporate a plurality of sprockets or the like for engaging the conveyor elements. The conveyor receives a plurality of plywood veneer strips or pieces 18 from a veneer dryer (not shown), which strips or pieces are deposited upon the conveyor proximate end shaft 16 and passed in the direction indicated by the arrows between the legs of a rectangular support table 20.

Table 20 carries therebeneath an upper elongated metal cabinet 22 disposed above the conveyor runs in crossways relation thereto, and a lower elongated metal cabinet 24 positioned between the conveyor runs and in parallel relation underneath cabinet 22. Table 20 also carries adjacent its rearward side a hood 26 supported from the table by bracket 28 and enclosing a marking means in the form of a sprayer 30 for marking veneer strips in which a predetermined amount of moisture is detected. The sprayer 30 is suitably provided with a paint shield 32 on the rearward side thereof and is otherwise similar to the spray head as disclosed in my aforementioned U.S. Pat. No. 4,377,783.

At the bottom of cabinet 22 and at the top of cabinet 24, a plurality of longitudinally oriented conducting metal plates are supported in facing relation to the veneer strips 18 conveyed therebetween. Lower cabinet 24 centrally supports transmitting plate 34 and phase plates 36 disposed in laterally spaced relation on either side of transmitting plate 34 and in the plane thereof, i.e. such that a piece of veneer 18 first passes over one of the phase plates 18, then transmitting plate 34, and then the remaining phase plate 36. In the specific example, plate 34 may have a width of approximately two inches and a length comparable to that of cabinet 24 so as to extend under the entire conveyor system. Phase plates 36 in the specific example are about one inch wide and are each spaced approximately one inch from transmitting plate 34. The phase plates 36 are also comparable in length to the length of the entire cabinet.

A receiving plate 38 is centrally supported from the underside of cabinet 22 and is suitably in substantial juxtaposition with plate 34, but somewhat narrower in this embodiment. In any case, plate 38 is desirably closer to plate 34 than to either plate 36. Plate 38 may have a width of about one and one-half inches and a length comparable to the length of cabinet 22. Grounding plates 40 are disposed on either side of plate 38 and in the plane thereof, each having a width of about one inch and each spaced about one inch from plate 38. Thus, plates 40 are in partial juxtaposition with plates 36 therebelow. Plates 40 are grounded to cabinet 22 and to the system or earth ground.

The arrays of plates suitably comprise printed or etched conductors on circuit board sections composed of epoxy glass and forming the top or the bottom of the respective cabinets. The printed circuit board is in each case mounted or potted in a polyester resin which provides an approximately one-eighth inch thick layer thereover, and is then mounted on the cabinet. Thus, the conducting plates are well insulated and protected from damage. The printed circuit boards are numbered 42 and 44.

The top runs 12 of the conveyor are positioned so that the strips 18 of veneer will be disposed approximately halfway between the transmitting and receiving plates. The veneer will frequently be quite narrow, i.e. a fraction of an inch, so that the top edge of run 12 will ordinarily be approximately halfway between the plates. The spacing between plates 34 and 38 is much wider and in a typical instance was approximately four and one-half inches. This spacing is suitable for measuring moisture in wood having a width from a fraction of an inch up to a width of about two inches, with the conveyor and/or cabinets 22 and 24 being adjusted so that the wood strips are approximately halfway between the plates as indicated above.

Referring to FIG. 3, a circuit is illustrated for the moisture detector according to the present invention. A signal transmitting means includes an alternating current signal source or oscillator 46, suitably comprising a type 12060 integrated circuit manufactured by Motorola. Oscillator 46 provides its output to a gate terminal of a VMOS field effect switching transistor, suitably comprising a type VN10KM, having a source terminal connected to a negative supply and a drain terminal connected to a positive supply via resistor 50.

The oscillator 46 suitably operates at frequency between one and two hundred kilohertz and via transistor 48 provides an input at that frequency to the primary winding 54 of one-to-four step-up transformer 52 having a secondary winding 56 and a Ferroxcube core. A voltage divider comprising resistors 58 and 60 is disposed between output terminals 62 and 64 of the transformer secondary wherein the center tap 98 between the resistors is grounded. The resistors have the same value such that equal and out-of-phase AC signals will be present at terminals 62 and 64 with respect to ground. Terminal 64 provides a transmitting signal to the aforementioned conducting plate 34. The signal at terminal 62, which is 180 degrees out-of-phase with the signal at terminal 64, is connected to phase plates 36.

Receiving plate 38 is adapted to receive the r.f. signal from transmitting plate 34, either directly or by way of a veneer strip 18. A receiving means, connected via lead 66 to receiving plate 38, includes a tuned circuit comprising parallel connected inductance 68 and capacitor 70 disposed between lead 66 and ground and tuned to substantially the frequency of oscillator 46. The signal across the tuned circuit is coupled by means of input resistor 72 to a first operational amplifier 74 provided with a feedback resistor 78 and a second input terminal which is grounded. The AC output of amplifier 74 is detected with diode 80 having its anode coupled to an input of comparator amplifier 86 through resistor 84 and shunted to ground through capacitor 82 in parallel with resistor 76. Amplifier 86 is provided with a second input terminal coupled via resistor 90 to the movable tap of a potentiometer 92 connected between a positive voltage and ground. The output terminal 94 of the detector circuit is coupled for operating sprayer 30 when a predetermined degree of moisture is detected in a particular veneer strip passing between the upper and lower plate arrays.

A received signal at plate 38 is amplified by amplifier 74 and detected by diode 30 to provide a negative voltage across capacitor 82. A second input of comparator amplifier 86 is set by means of potentiometer 92 to establish a threshold such that if the negative charge on capacitor 82 drops below a predetermined level, the output at terminal 94 will, via intermediate amplifiers not shown, operate sprayer 30. That is, moisture is ordinarily indicated when the negative voltage on capacitor 82 decreases. Feedback resistor 88 produces a hysteresis effect such that once the sprayer starts to operate, it will continue to do so until the negative voltage across capacitor 82 increases to a negative value greater than the value at which spraying started, whereby erratic or intermittent operation of the sprayer is prevented.

Considering the overall operation of the moisture detecting apparatus illustrated in FIGS. 1 through 3, the alternating current signal on transmitting plate 34 is normally coupled to receiving plate 38 in the absence of wet veneer or other conducting material in the general area therebetween, indicated by dashed line 18' in FIG. 3. The signal received at plate 38 is minimized somewhat by the out-of-phase signals coupled from plates 36 on either side of plate 34. However, plate 34 is positioned closer to plate 38 and a net signal will be received and detected by the receiving circuitry to provide a negative charge across capacitor 82 by way of diode 80. Potentiometer 92 is set such that an output will not be produced at terminal 94 at this time as would operate a sprayer.

In the presence of wet veneer between the arrays of plates, i.e. at the position indicated at 18' in FIG. 3, moisture that extends substantially across transmitting plate 34 and one or both of the phase plates 36 has a shunting effect on the transmitted signal such that a decreased signal is received at receiving plate 38, causing the negative voltage on capacitor 82 to decrease or become more positive whereby the comparator amplifier 86 produces a signal output at terminal 94 for operating the sprayer and marking the wood. Of course, potentiometer 92 can be adjusted to select the correct point at which the sprayer is operated.

Wet veneer at position 18' provides a shielding effect relative to receiving plate 38, or a shunting effect such that the signal field from plate 34 tends to pass from plate 34 to phase plates 36, whereby the signal at plate 38 is reduced in the presence of wet material. Viewed in another manner, the phase plates 36, in the presence of wet wood, tend to cancel out the signal of the transmitting plate in the wood whereby the net potential at the wood is approximately zero or ground level, i.e. halfway between the signal levels of plate 34 and plates 36. Since the wood strip is at ground level, or the point of reference return for the receiving means, the receiving means is little affected by the position of the wood. That is, a given piece of wood can be warped or thicker so as to place it closer or farther away from the receiving plate, and the same or approximately the same result in signal reduction at the receiving plate is achieved, substantially regardless of the vertical position of the wet wood.

Not only is the device substantially independent of position of the wood, but is also substantially independent of the grounding or non-grounding of the wood through some other means. Thus, it will frequently occur that the moist wood will become grounded to a metal conveyor or the like and such grounding would have a deleterious effect on the accuracy of measurement in prior art moisture detectors. However, in the present instance where a virtual ground level is induced in the moist wood by the plate 34-36 combination, additional grounding of the wood at some point has no effect. As a matter of fact, to determine whether the apparatus according to the present invention is working properly, a moist strip of veneer is purposely grounded to determine whether any effect is produced in the output signal at 94. If no effect is produced, the circuit is in proper adjustment.

According to an alternative embodiment, the veneer strip is continuously grounded as indicated in 96 at FIG. 3 by means of a grounded roller, grounded metal conveyor or the like whereby a shielding ground potential is provided on veneer strip 18' without requiring the use of phase plates 36. However, the principal embodiment of the present invention including phase plates 36 is preferred because good physical contact with the moist veneer is then not required and the entire measuring sequence can be accomplished without requiring any contact with the veneer. Therefore, irregular or intermittent operation caused by a poor contacting roller or conveyor is avoided.

The grounding plates 40 help maintain a zero or low signal condition on receiving plate 38 in the absence of direct or non-shielded coupling from transmitting plate 34. Thus, they tend to shield the receiving plate 38 from the fields of plates 36, and shunt undesired signals to ground. Also, if the veneer passes very close to the receiving plate array, the plates 40 help shunt undesired signal gradients as may be present on such veneer strips. It should also be noted that both the cabinets 22 and 24 are grounded for the purpose of shielding the plate arrays from external influence.

The embodiment illustrated in FIGS. 1-3, and particularly as shown in FIG. 1, depicts a cross chain arrangement providing cross flow of veneer strips, i.e. with their long dimension transverse to the direction of conveyor movement. A particular veneer strip 18 passing through the conductive plate arrays will be spray painted on one end as indicated at 100 in FIG. 1 to mark the veneer strip so that it may be segregated from others. Longitudinal feed is also possible, for example as illustrated in my aforementioned U.S. Pat. No. 4,377,783 where the conveyors conveniently comprise roller means. In that case, veneer strips will pass between the plate arrays in parallel fashion, with several strips, laterally spaced from one another, passing through at the same time. In accordance with the variation of my invention illustrated in FIG. 4, an upper cabinet 22' is provided which is substantially the same as cabinet 22 in FIG. 2, except that the receiving plate is segmented into sections 38a, 38b, 38c, 38d, 38e, etc., along the length of the cabinet. Each segment has associated therewith a separate detector circuit and sprayer means so that various parallel strips passing through can be separately detected as to moisture content and marked accordingly. The strips 38b, 38c and 38d have edges adjacent one another which are diagonal to the direction of veneer movement in order to provide some overlap in detector coverage. The space between segments 38a and 38b, as well as the space between segments 38d and 38e are straight, representing the ends of circuit board sections from which the plate array is constructed and suitable for juxtaposition with a conveyor chain, if this type of conveying means is used. The length of the segments are comparable to, or less than, the width of veneer strips.

Referring to FIGS. 5 and 6, a further modification of the apparatus according to the present invention is illustrated wherein the use of a structural conveyor between the arrays of plates is avoided. Instead, an air cushion is generated which supports the veneer strips as they pass between the plates. Referring to the drawings, the upper part of cabinet 24' is provided with an air chamber 102 to which air under pressure is delivered by way of conduit 104. An air pressure of about 2 or 3 psi is sufficient. The circuit board 42' at the top of cabinet 24' is suitably formed of fiberglass in which a plurality of holes 106 have been drilled, wherein these holes, proceeding upwardly, slant forwardly in the direction of desired conveyor movement at an angle of between 45° and 70° with the horizontal. An angle of about 50° to 60° is preferred. These holes are suitably approximately ⅛" in diameter and are positioned at approximately 1"

centers in both directions across the circuit board 42'. The airflow supports the veneer strips 18 without the requirement of a metal conveyor or the like, and also transports the veneer strips forwardly in the direction indicated by the arrow. Typically, the veneer will be supported on an air cushion about ⅛" above circuit board 42'. Again, the spacing between circuit boards 42' and 44 is about 4", and the thickness of the veneer is small with respect to the spacing between the plate arrays. It will be understood that the veneer strips 18 will be delivered to the region of cabinets 22 and 24' by conventional conveyor means not shown, and delivered to conveyor means also not shown.

While the measurement of moisture in veneer is particularly set forth herein, it will be understood that the method and apparatus is not restricted thereto but is applicable to other materials.

It will also be appreciated the transmitting and receiving plates can be reversed either position-wise or circuit-wise.

While we have shown and described plural embodiments of our invention, it will be apparent to those skilled in the art that many changes and modifications may be made without departing from our invention in its broader aspects. We therefore intend the appended claims to cover all such changes and modifications as fall within the true spirit and scope of our invention.

We claim:

1. The method of measuring the moisture content of material comprising:
   passing a radio frequency signal across a region wherein said material is to be received and ascertaining the magnitude of the signal thus coupled,
   passing said material through said region,
   shunting away a portion of said signal in a direction along said material in accordance with the moisture contained therein,
   and ascertaining the change in the signal coupled across said region to determine the extent of said moisture.

2. The method according to claim 1 further comprising marking said material if the change indicating moisture content exceeds a predetermined value.

3. Apparatus for measuring the moisture content of material, said apparatus comprising:
   first transmitting conductor means disposed in facing relation to said material,
   second receiving conductor means disposed in facing relation to said material on the opposite side of said material from said first conductor means,
   transmitting means and receiving means,
   means for connecting said transmitting conductor means to said transmitting means and means for connecting said receiving conductor means to said receiving means,
   third conductor means in coupling relation to said material and providing a shunting path relative to said transmitting means to subtract from signal passage between said first and second conductor means according to the moisture in said material that extends at least between the first conductor means the the third conductor means,
   and means for detecting the change in signal passage to detect said moisture.

4. The apparatus according to claim 3 wherein said first and second conductor means are in generally facing juxtaposition on either side of said material.

5. The apparatus according to claim 4 wherein said third conductor means is spaced from the area of juxtaposition of said first and second conductor means.

6. The apparatus according to claim 3 wherein said third conductor means contacts said material.

7. The apparatus according to claim 3 wherein said third conductor means is in spaced relation to said material and assymetrically spaced with respect to said first and second conductor means.

8. The apparatus according to claim 7 including means for connecting said third conductor means in out-of-phase relation with one of the other of said conductor means.

9. The apparatus according to claim 8 wherein said means for connecting said third conductor means in out-of-phase relation provides a potential value to balance the potential provided by said one of the other of said conductor means in said material to place the moisture in said material at substantially ground potential.

10. Apparatus for measuring the moisture content of material, said apparatus comprising:
    a first conductor plate disposed in facing relation to said material,
    a second conductor plate disposed in facing relation to said material on the opposite side of said material from said first conductor plate and in generally facing juxtaposition to said first conductor plate,
    transmitting means and receiving means,
    means for connecting one of said plates to said transmitting means to be energized thereby and means for connecting the other of said plates to said receiving means for registering a signal,
    a third conductor plate disposed in facing relation to said material on the same side of said material as said first plate, in laterally spaced relation from said first plate, and out of primary juxtaposition with said second plate, such that said first plate is more closely spaced to said second plate than is said third plate,
    and means for connecting said first and third plates in out-of-phase relation whereby moisture in said material is disposed in shunting relation between said first and third plates to subtract from signal passage between said first and second plates so that moisture can be detected according to the change in signal passage.

11. The apparatus according to claim 10 including conveyor means for moving said material between said plates.

12. The apparatus according to claim 11 wherein said conveyor means includes a plurality of air passages underneath said material and an air supply therefor for providing air pressure upwardly through said passages.

13. The apparatus according to claim 12 wherein said air passages slant forwardly in the direction of desired conveyor movement, as they pass upwardly, for moving said material forwardly.

14. The apparatus according to claim 10 further including marking means for marking said material in response to a detection of moisture.

15. The apparatus according to claim 10 wherein said second plate is segmented, and further including marking means associated with each second plate segment for marking the said material adjacent such segment for which moisture is detected.

16. The apparatus according to claim 10 wherein said material is thin as compared with the distance between said first and second plates, said third plate being on substantially the same level as said first plate.

17. The apparatus according to claim 10 including means for passing material between said first and second plates, said material first passing adjacent said third plate, and an additional third plate coupled to the first mentioned third plate and adjacent which said material passes after passing between said first and second plates, said third plates being on substantially the same level as said first plate.

18. The apparatus according to claim 17 further including a pair of fourth plates adjacent and substantially on the same level as said second plate, said fourth plates being respectively disposed in substantial juxtaposition with said third plates, and means for coupling said fourth plates to a common reference potential.

19. The apparatus according to claim 10 wherein said second plate is narrower than said first plate.

20. The apparatus according to claim 19 wherein said second plate is connected to said receiving means and wherein said first plate is connected to said transmitting means.

21. Apparatus for measuring the moisture content of material, said apparatus comprising:
  a radio frequency input electrical signal driven element including plural electrically conductive driven portions, each of said driven portions being connected to one of two sources of input electrical signal of opposed phase;
  a receptor element in a substantially fixed relation with respect to said driven element including an electrically conductive active area; and
  means for positioning said material between and adjacent said driven element and said receptor element such that said material is disposed to effectively shield said active area from electrostatic coupling with said driven element portions when said material has a degree of dampness and to less effectively shield said said active area from electrostatic coupling with said driven element portions when said material has less than said degree of dampness.

22. Apparatus as in claim 21 wherein said radio frequency input electrical signal is on the order of 100 kHz or more.

23. Apparatus as in claim 21 wherein said receptor element and said driven element are separated by a distance sufficient to allow said material up to two inches thick to be positioned therebetween.

24. Apparatus for measuring the moisture content of material, said apparatus comprising:
  first conductor means disposed in facing relation to said material,
  second conductor means disposed in facing relation to said material on the opposite side of said material from said first conductor means,
  transmitting means and receiving means,
  means for connecting one of said conductor means to said transmitting means to be energized thereby and means for connecting the other of said conductor means to said receiving means for registering a signal,
  third conductor means disposed in facing relation to said material on the same side of said material as said first conductor means and in laterally spaced relation from said first conductor means, said first conductor means being more closely spaced to said second conductor means than is said third conductor means,
  and means for connecting said first and third conductor means in out of phase relation whereby moisture in said material is disposed in shunting relation between said first and third conductor means to subtract from signal passage between said first and second conductor means so that moisture can be detected according to the change in signal passage.

25. Apparatus for measuring the moisture content of material, said apparatus comprising:
  first conductor means disposed in facing relation to said material,
  second conductor means disposed in facing relation to said material on the opposite side of said material from said first conductor means,
  third conductor means disposed in facing relation to said material on the same side of said material as said first conductor means and in laterally spaced relation from said first conductor means but wherein said first conductor means is more closely spaced to said second conductor means than is said third conductor means,
  a signal source and means for coupling said signal source to said conductor means to provide signal passage between said second conductor means on one side of said material and said first and third conductor means on the opposite side of said material,
  means for connecting said first and third conductor means in out-of-phase relation so that moisture in said material provides a shunting signal pathway between said first and third conductor means subtracting from signal passage between said first and second conductor means,
  and means for detecting the change in signal passage.

* * * * *